United States Patent [19]

Scott et al.

[11] Patent Number: 5,032,283

[45] Date of Patent: * Jul. 16, 1991

[54] LOW DISPERSION FLUID CONDUIT USEFUL IN CHROMATOGRAPHY SYSTEMS

[75] Inventors: Raymond P. W. Scott, Ridgefield; Elena Katz, Westport, both of Conn.

[73] Assignee: The Perkin Elmer Corporation, Norwalk, Conn.

[*] Notice: The portion of the term of this patent subsequent to May 20, 2003 has been disclaimed.

[21] Appl. No.: 882,017

[22] Filed: Jul. 3, 1986

Related U.S. Application Data

[63] Continuation of Ser. No. 676,971, Nov. 30, 1984, abandoned, which is a continuation of Ser. No. 471,910, Mar. 3, 1983, abandoned.

[51] Int. Cl.$^5$ .............................................. B01D 15/08
[52] U.S. Cl. ................................. 210/656; 210/198.2
[58] Field of Search ............... 210/656, 198.2; 55/67, 55/386; 436/161; 422/70; 73/61.1 C

[56] References Cited

U.S. PATENT DOCUMENTS

| | | | |
|---|---|---|---|
| 3,784,467 | 1/1974 | Tanimura et al. | 210/198.2 |
| 3,796,657 | 3/1974 | Pretorius | 210/656 |
| 3,820,660 | 6/1974 | Halasz et al. | 210/198.2 |
| 4,234,427 | 11/1980 | Boehme | 210/198.2 |
| 4,269,710 | 5/1981 | Hunt | 210/198.2 |
| 4,293,419 | 10/1981 | Bente, III et al. | 210/198.2 |
| 4,389,313 | 6/1983 | Charney | 210/198.2 |
| 4,410,507 | 10/1983 | Chia | 530/363 |
| 4,414,108 | 11/1983 | Ito | 210/198.2 |
| 4,424,127 | 1/1984 | Roeraade | 210/198.2 |
| 4,448,691 | 5/1984 | Davis | 210/656 |
| 4,450,082 | 5/1984 | Tanouchi | 210/656 |
| 4,500,430 | 2/1985 | Dasgupta | 210/656 |
| 4,582,608 | 4/1986 | Ritacco | 210/656 |
| 4,589,477 | 5/1986 | Scott | 422/161 |
| 4,627,918 | 12/1986 | Saxena | 210/656 |

OTHER PUBLICATIONS

Robbins & Myers advertisement in Chemical Engineering, Jun. 12, 1961, p. 163.
"Axial Dispersion and Flow Phenomena in Helically Coiled Tubular Reactors for Flow Analysis and Chromatography", R. Tijssen, Analytica Chimica Acta, 114 (1980), pp. 71–89.
"Mass Transfer in Ideal and Gerometrically Deformed Open Tubes; I. Ideal and Coiled Tubes with Circular Cross-Section", D. Hofmann & I. Halasz, Journal of Chromatography, 173 (1979), pp. 221–228.
"Mass Transfer in Ideal and Geometrically Deformed Open Tubes; II. Potential Application Ideal and Coiled Open Tubes in Liquid Chromatography", I. Halsz, Journal of Chromatography, 173 (1979), pp. 229–247.
"Mass Transfer in Ideal and Geometrically Deformed Open Tubes; III. Deformed Metal and Plastic Tubes", K. Hofmann & I. Halasz, Journal of Chromatography, 199 (1980), pp. 3–22.
"Dispersion Phenomena in Reactors for Flow Analysis", J. Van Den Berg, R. Deelder & H. Egberink, Analytica Chimica Acta, 114 (1980), pp. 91–104.

Primary Examiner—Ernest G. Therkorn
Attorney, Agent, or Firm—Thomas P. Murphy; Edwin T. Grimes

[57] ABSTRACT

A fluid conduit including a tube having a two-dimensional serpentine opening therethrough and exhibiting low peak dispersion is applicable as an extra-column connection.

2 Claims, 1 Drawing Sheet

LOW DISPERSION FLUID CONDUIT USEFUL IN CHROMATOGRAPHY SYSTEMS

This application is a continuation of application Ser. No. 676,971, filed on Nov. 30, 1984, which, in turn, is a continuation of application Ser. No. 471,910, filed Mar. 3, 1983, both now abandoned.

BACKGROUND OF THE INVENTION

The present invention generally relates to a fluid conduit and, in particular, relates to a fluid conduit having a two-dimensional serpentine opening therethrough.

A well known fluid flow characteristic of a straight conduit is the formation of a parabolic-shaped velocity front. This is a consequence of the peripheral fluid being reduced along its interface with the inner surface of the conduit. This flow retardation is transferred, with lessening effect with distance, toward the central portion of the fluid. Hence, any given cylindrical band of fluid entering a conduit with a planar front is lengthened due to this phenomena. In chromatography this is generally referred to as band dispersion.

Until recently, the chromatographer was predominantly concerned with band dispersion which occurred within the separation column and, to a lesser extent, the band dispersion in the extra-column connecting conduits. However, recent developments in column technology have forced more attention on the effects of extra-column dispersion and the reduction thereof. Extra-column dispersion can introduce unacceptable band, and subsequently peak, broadening both before and after the separating columns.

In the pre-column conduits band dispersion disrupts the planar front of the sample mixture and results in the sample mixture being injected onto the column in a non-uniform concentration. Band dispersion in post-column conduits, such as conduits between the column and the detector, tend to spread each separated component and, by such spreading, cause separated components to overlap. This overlapping results, for all intents and purposes, in a remixing of the previously separated sample components. Consequently, in modern low dispersion chromatography systems, the band dispersion of extra-column connecting conduits is a major consideration.

In general, one approach to reducing dispersion in a fluid conduit is to make the conduit both short and of a small inside diameter. However, such conduits are quite easily plugged and further they are unnecessarily inconvenient in the arrangement and operation of a chromatographic system.

SUMMARY OF THE INVENTION

Accordingly, it is one object of the present invention to provide a fluid conduit useful for chromatography systems which exhibits a minimal band dispersion.

This object is achieved, at least in part, by providing a tube which defines a two-dimensional serpentine opening therein.

Other objects and advantages will become apparent to those skilled in the art from the following detailed description read in conjunction with the accompanying drawing and the claims appended hereto.

BRIEF DESCRIPTION OF THE DRAWING

The drawing, not drawn to scale, includes.

DETAILED DESCRIPTION OF THE INVENTION

Figure 1:
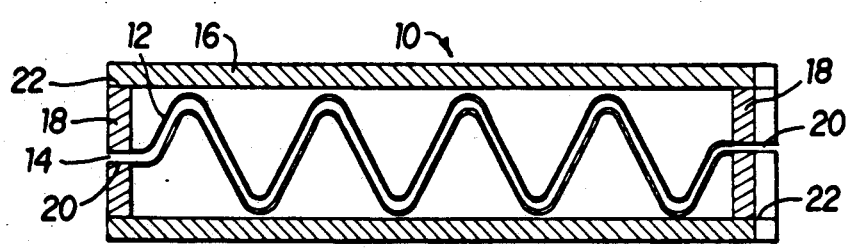
FIG. 1, which is a cross-sectional view of a conduit embodying the principles of the present invention.
Figure 2:
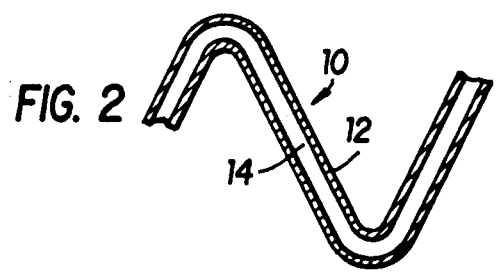
FIG. 2 is an exploded view of a segment of the conduit shown in FIG. 1.

A fluid conduit, indicated generally at 10 in FIGS. 1 and 2, and embodying the principles of the present invention, includes a tube 12, having a continuous opening 14 therethrough. The tube 12 is shaped such that the opening is a two-dimensional serpentine. As used herein the term "serpentine" is taken to mean a continuously curving path having periodic peaks and valleys of substantially uniform amplitude. As a consequence of the serpentine path, it is understood that the radial velocity of a fluid passing through the serpentine path is continuously changing in magnitude as well as periodically reversing direction. In the preferred embodiment, the tube 12 is secured within a conventionally sized conduit 16 so as to conveniently introduce the tube 12 into a fluid path of a conventional system.

In the preferred embodiment the tube 12 is stainless steel and has an outside diameter of about 0.5 millimeters (about 0.02 inch) and an inside diameter of about 0.25 millimeters (about 0.01 inch).

A length of about 42.5 centimeters of the tube 12 is formed into a serpentine which has a longitudinal distance between adjacent peaks of about 1.8 millimeter and a transverse distance between adjacent peaks of about 0.5 millimeter. As seen in FIGS. 1 and 2, the adjoining sections of the serpentine extend in opposite directions and interconnect at an acute angle. Such a serpentine path results in a total longitudinal length of about 38 centimeters. The formation of the serpentine may be accomplished by techniques known in the art, for example, the tube 12 can be fed between a pair of complementary-shaped gears in a manner similar to that of feeding cloths through a wringer. The serpentine opening 14 should be formed so that a uniform cross-section is maintained for the length of the tube 12. In this manner, the possibility of the opening 14 becoming plugged is substantially completely eliminated in most liquid chromatography applications.

In order to use the above-described tube 12 in a conventional liquid chromatography system the tube 12 is secured within a length of conventionally sized conduit 16, i.e., such as one having an inside diameter of about 1.3 millimeters and an outside diameter of about 1.6 millimeters. Although any means can generally be employed to accomplish this, it is preferred to attach a disk 18 having an opening 20 therethrough to the tube 12. In one embodiment a pair of disks 18 each having a thickness of about 1 millimeter, having a central opening 20 of about 0.5 millimeter and an outside diameter of about 1.6 millimeter were used. The disks 18 were attached to each end of the tube 12 by well known techniques, such as soldering. Thereafter, the disks 18 were secured to the ends 22 of the conduit 16, also by soldering.

So far as it is understood, a fluid conduit 10 formed in accordance with the above-described preferred embodiment exhibits an insignificant band dispersion. The reason for this is believed to be the inability of the flowing fluid to set up a parabolic wavefront flow at any point along the serpentine. This type of flow is prevented because of the continuously curving nature of the opening 14 which causes the radial velocity to continuously change and reverse direction. Further, above a minimal flow rate, i.e., less than 1 milliliter per minute, the flow at all points within the serpentine is in the nature of a continuous radial flow with little or no contribution from laminar flow.

In the following discussion of FIGS. 3A and 3B, which are comparative studies between a conduit embodying the principles of the present invention and two different conventional fluid connecting tubes, the variance of peak ($\sigma^2$) is used as the comparative basis.

This factor was chosen because an ideal chromatographic peak is Gaussian, or bell-shaped, in nature and from a mathematical standpoint it is not the standard deviation ($\sigma$) but its square ($\sigma^2$), the variance, which is the basic measure of a normal distribution. Further, to allow a more explicit comparison, the variance ($\sigma^2$) has been normalized with respect to length. Hence, the ordinate axis is designated as variance per unit length ($\sigma^2/l$) which for chromatographic purposes has the units of microliter squared per centimeter ($\mu L^2/cm$). The other comparative variable is the flow rate, as plotted along the abscissa and which is expressed in units of milliliters per minute (mL/min.).

Figure 3A:
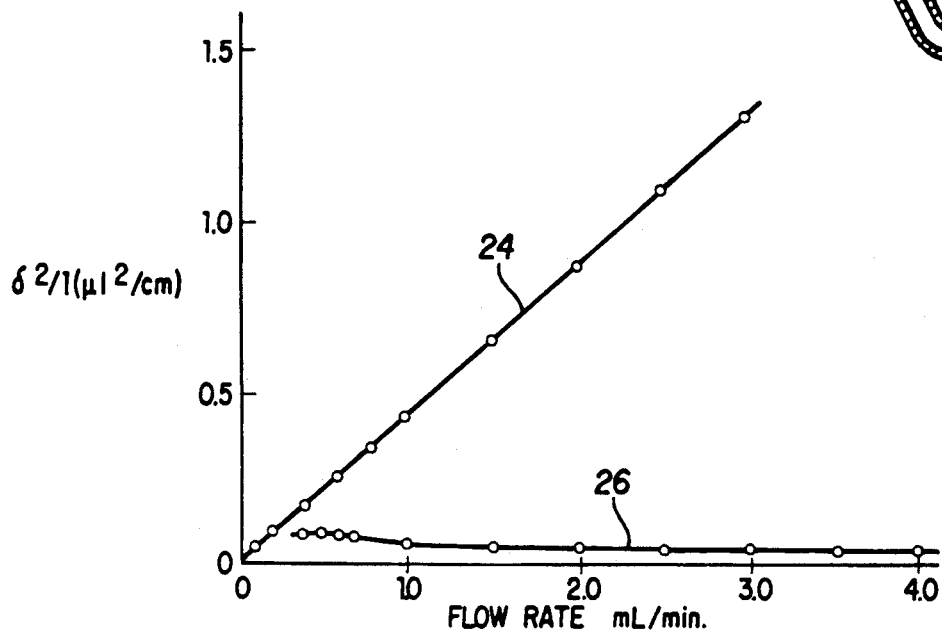
FIGS. 3A and 3B are comparative graphs demonstrating the reduced dispersion of the conduit shown in FIG. 1.

Referring specifically to FIG. 3A, the straight line plot 24 is the normalized peak variance versus flow rate for a straight tube having about a 0.18 millimeter (0.007 inch) inside diameter. The plot 26 is the graph for a conduit designed according to the principles of the present invention and having an inside diameter of about 0.25 millimeters (0.01 inch).

Figure 3B:
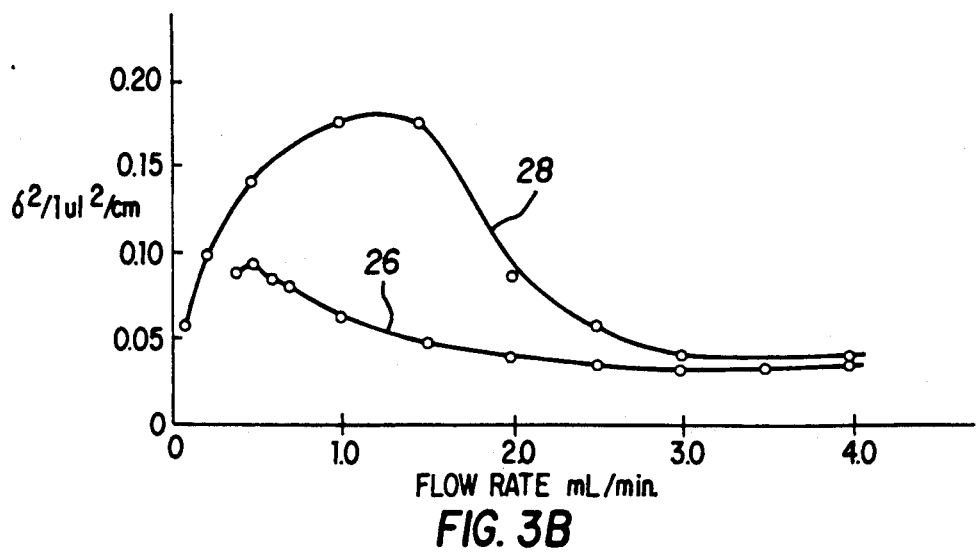

Referring to FIG. 3B the graph 26 is compared with a coiled tube having an inside tube diameter of about 0.13 millimeter and a coil diameter of about 1 millimeter, represented by graph 28.

From these comparisons it is clear that the fluid conduit 10 is significantly better than a straight tube, the variance of which, over the flow range examined, increases quite linearly with flow rate. This linear increase can clearly be seen as having an unfavorable extra-column effect or dispersion even when the inside diameter of the conduit is less than that used in the fluid conduit 10 of the present invention. Further, although the variance of the herein described conduit 10 is approached by the coiled tube at high flow rates, the coiled tube has a significantly higher variance at flow rates of about 1 milliliter/minute. From a close analysis of the results of experiments performed to date, a variance of about 0.04 $\mu L^2$/centimeter is readily achieved by conduits embodying the principles of the present invention. Thus, it is clear that a fluid conduit embodying the principles of the present invention can provide a performance hitherto unattainable.

Consequently, a fluid conduit 10 such as described herein can be used as a connecting tube exhibiting low dispersion in a liquid chromatography system. That is, such a conduit has application as a connecting tube, as, for example, between an injection valve and a separation column or between the column and a detector cell. Further, because of the radial flow inherent therein, such a conduit can also be advantageous as a mixing device.

Although the present fluid conduit has been described in a specific embodiment other arrangements and uses will become apparent to those skilled in the art. Consequently, the description presented herein is deemed exemplary and the invention is deemed limited by the claims and the reasonable interpretation thereof.

What is claimed is:

1. A method for conducting liquid from a first point to a second point along a flow path in a chromatographic system so as to induce nonlaminar flow and avert band dispersion at the second point comprising the steps of:

passing the liquid along said flow path at a predetermined flow rate, said flow rate being within the range of 1.0 to 2.0 milliliter/minute, substantially continuously varying the magnitude of the radial velocity of the liquid as it flows from the first point to the second point, periodically abruptly reversing the direction of flow of the liquid as it flows from the first point to the second point, the period of abrupt reversal of flow being generally constant, and restricting the distance of flow of the liquid between said periodic reversals to less than the required for substantial formation of a band-dispersive parabolic wavefront at the predetermined flow rate.

2. The method of claim 1 wherein the liquid is conducted for from the first point to the second point substantially in a plane.

* * * * *